(12) United States Patent
Bae et al.

(10) Patent No.: US 12,419,687 B2
(45) Date of Patent: Sep. 23, 2025

(54) NASAL IMPLANT DESIGN METHOD OF MANUFACTURING PATIENT-CUSTOMIZED NASAL IMPLANT

(71) Applicant: BISTOOL INC., Seoul (KR)

(72) Inventors: Eun Hyun Bae, Seoul (KR); Seo Won Yang, Seoul (KR)

(73) Assignee: BISTOOL INC., Seoul (KR)

( * ) Notice: Subject to any disclaimer, the term of this patent is extended or adjusted under 35 U.S.C. 154(b) by 995 days.

(21) Appl. No.: 17/393,786

(22) Filed: Aug. 4, 2021

(65) Prior Publication Data
US 2022/0039867 A1 Feb. 10, 2022

(30) Foreign Application Priority Data

Aug. 6, 2020 (KR) .......................... 10-2020-0098629
Oct. 27, 2020 (KR) .......................... 10-2020-0140187

(51) Int. Cl.
*A61B 34/10* (2016.01)
*G06N 20/00* (2019.01)

(52) U.S. Cl.
CPC .............. *A61B 34/10* (2016.02); *G06N 20/00* (2019.01); *A61B 2034/104* (2016.02); *A61B 2034/105* (2016.02); *A61B 2034/108* (2016.02)

(58) Field of Classification Search
CPC .............. A61B 34/10; A61B 2034/104; A61B 2034/105; A61B 2034/108;
(Continued)

(56) References Cited

U.S. PATENT DOCUMENTS 11,564,793 B2 * 1/2023 Baek ..................... A61F 2/186
2020/0211698 A1 * 7/2020 Douglas ................. G16H 50/50

FOREIGN PATENT DOCUMENTS

JP       H0935091 A   *  2/1997
KR   20160024894 A   *  3/2016
(Continued)

OTHER PUBLICATIONS

Kim Breitfelder; Don Messina. "IEEE 100 the Authoritative Dictionary of IEEE Standards Terms" (IEEE Press, 2000): 100-2000. ISBN 0-7381-2601-2. (Year: 2000).*
(Continued)

*Primary Examiner* — Juan C Ochoa
(74) *Attorney, Agent, or Firm* — Mendelsohn Dunleavy, P.C.

(57) ABSTRACT

Proposed is a nasal implant design method of manufacturing a patient-customized nasal implant; the nasal implant design method including: (a) acquiring a medical image of a patient's nasal portion; (b) automatically realizing a three-dimensional volume rendering image, including the skin, the bones, and the cartilage of a nasal portion, from the medical image of the patient's nasal portion on the basis of nasal cartilage data learned through artificial intelligence; (c) simulating the nasal cartilage with the three-dimensional volume rendering image in such a manner as to be suitable for a patient; (d) stably nesting a nasal implant selected from an imaginary nasal implant model database on the simulated nasal cartilage and a nasal bones; and (e) simulating the stably nested nasal implant and designing a patient-customized nasal implant in such a manner as to be suitable for the patient.

11 Claims, 12 Drawing Sheets

(58) Field of Classification Search
CPC .............. A61B 2034/102; G06N 20/00; A61F 2240/002; A61F 2/186; A61F 2/0059; A61F 2002/30948; A61F 2/30756; A61F 2/30942; A61F 2002/3096; G06T 17/00; G16H 30/20
USPC .......................................................... 703/1
See application file for complete search history.

(56) References Cited

FOREIGN PATENT DOCUMENTS

| KR | 20170096344 A | * | 8/2017 |
| KR | 20170096345 A | * | 8/2017 |
| KR | 200489594 Y1 | * | 7/2019 |

OTHER PUBLICATIONS

Choi, Yim Don, Youngjun Kim, and EunSoo Park. "Patient-specific augmentation rhinoplasty using a three-dimensional simulation program and three-dimensional printing." Aesthetic Surgery Journal 37, No. 9 (2017): 988-998. (Year: 2017).*

Wang, Jing-xiao, Sheng-hui Liao, Xing-hao Zhu, Ying Wang, Chong-xiang Ling, Xi Ding, Yi-ming Fang, and Xiu-hua Zhang. "Real time 3D simulation for nose surgery and automatic individual prosthesis design." Computer methods and programs in biomedicine 104, No. 3 (2011): 472-479. (Year: 2011).*

Xie, Kai, and Yue Min Zhu. "Interactive surgery simulation for the nose augmentation using CT data." Neural Computing and Applications 19 (2010): 61-65. (Year: 2010).*

Gao, Jianlin, et. al. "Three dimensional surface warping for plastic surgery planning." In 2001 IEEE International Conference on Systems, Man and Cybernetics. e-Systems and e-Man for Cybernetics in Cyberspace (Cat. No. 01CH37236), vol. 3, pp. 2016-2021. IEEE, 2001 (Year: 2001).*

Manuel, Cyrus T., Ryan Leary, Dmitriy E. Protsenko, and Brian JF Wong. "Nasal tip support: a finite element analysis of the role of the caudal septum during tip depression." The Laryngoscope 124, No. 3 (2014): 649-654. (Year: 2014).*

* cited by examiner

FIG. 10
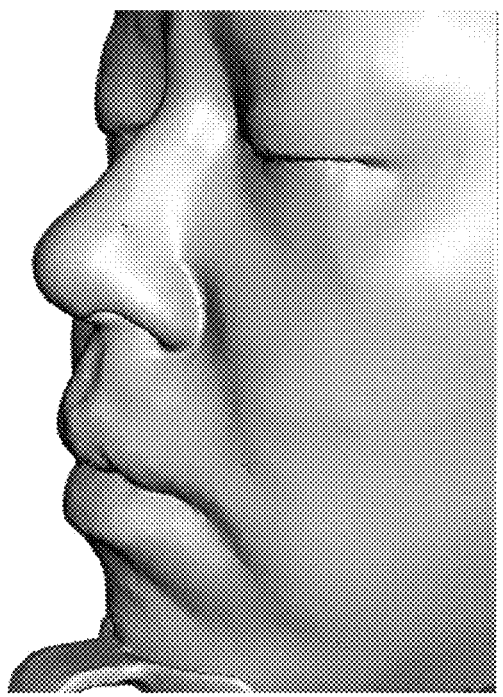 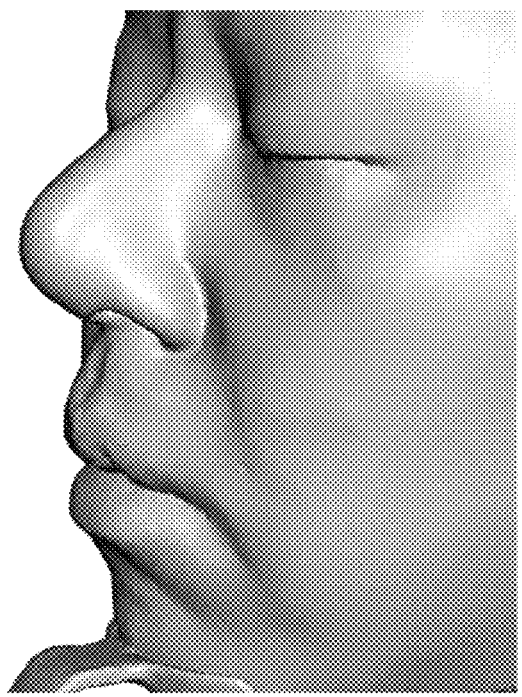

FIGURE 11

A nasal implant design method of manufacturing a patient-customized nasal implant, the nasal implant design method comprising steps (a)-(f), wherein step (a) comprises (a) acquiring a CT or CBCT image of a patient's nasal portion using low-dose radiation exposure (b) Automatically realizing a three-dimensional volume rendering image, including skin, bones, and cartilage of the nasal portion, on the basis of nasal cartilage data learned through artificial intelligence for predicting the nasal cartilage from the medical image of the patient's nasal portion on the basis of the nasal cartilage data learned through a deep learning scheme using medical images resulting from high-dose radiation exposure from which the nasal cartilage is visible (c) Simulating the nasal cartilage with the three-dimensional volume (d) Stably nesting a nasal implant selected from a virtual nasal implant model database on the simulated nasal cartilage and the nasal bones (e) Simulating the stably nested nasal implant and designing a patient-customized nasal implant (f) Cutting an arbitrary surface of the patient-customized nasal cartilage and verifying whether or not the patient-customized nasal cartilage is perfectly brought into contact with the simulated nasal cartilage and the nasal bones; and (g) Automatically computing and displaying a change in a height of a skin surface of the nasal portion with respect to the patient-customized nasal implant.

Wherein Step (c) the simulating of the nasal cartilage of FIG. 11 comprises steps (c-1), (c-2) and (c-3) in any order, followed by step (c-4) as follows:

Wherein Step (d) the stable nesting of the nasal cartilage of FIG. 11 comprises steps (d-1), (d-2) and (d-3) as follows:

NASAL IMPLANT DESIGN METHOD OF MANUFACTURING PATIENT-CUSTOMIZED NASAL IMPLANT

BACKGROUND OF THE INVENTION

Field of the Invention

The present disclosure relates to a nasal implant design method of manufacturing a patient-customized nasal implant and, more particularly, to a method of designing a nasal implant through an adjustment to a cartilage operation that is based on nasal cartilage data learned through artificial intelligence.

Description of the Related Art

A nose is part of the respiratory system and is also a sensory organ responsible for the olfactory sense. As an anatomical feature, the nose projects above the mouth on the face and has a nasal cavity inside. FIG. 1 is a view illustrating an anatomical structure of the nose. With reference to FIG. 1, the nasal bones extending from the middle of the forehead to the bridge of the nose accounts for approximately one-third of the nose, and the upper lateral cartilage and the lower lateral cartilage that extend from the bridge of the nose to the end of the nose cover approximately two-thirds of the nose. The basal bone and the upper lateral cartilage partially overlap.

A nasal implant is inserted into an upper portion of the nasal cartilage and thus alters the shape of the nose. In recent years, personal and social concerns with personal outward appearance have increased, and thus a plastic surgery operation has been prevalent. In the related art, CT data on a patient are used to design a nasal implant. However, shapes of the nasal bones can be realized using CT scans, but a cartilage portion cannot be identified. A shape of the end of the nose in which a cartilage is positioned is a particularly important factor in nasal surgery. Thus, there have been numerous studies conducted on manufacturing of the nasal implant based on arbitrary design of the cartilage through structures of the nasal bones and the nasal cavity that are known through the existing CT data.

For example, Korean Patent Application Publication No. 10-2019-0131796 (Patent Document 1) directed to a method of manufacturing a nasal implant discloses that three-dimensional images of the skin, the nasal bones, and the nasal cavity are acquired using a segmentation method by adjusting a Housefield Unit (HU) value in a CT image of a nasal portion, and then the nasal cartilage is designed on the basis of the acquired three-dimensional images (refer to the paragraph Nos. [0029] and [0030]). In this segmentation job, triangle mesh data on the skin, the nasal bones, and the nasal cavity are extracted from CT raw data, the extracted triangle mesh data are corrected, cartilage data are plotted, and then a nasal implant is designed. However, when using a triangle extraction method (marching cubes), a hole, a long triangle, a wrongly connected triangle, or the like may occur in a triangle mesh. Thus, a correcting process or a smoothing and filling-up process needs to be performed. These processes may increase the likelihood of error. In addition, smoothing of an extracted mesh (a Poisson process) refers to a process that averages positions of a mesh using positional information on various triangles attached on the mesh itself. The result of this process is somewhat from that of a process of smoothing a voxel using an average value of nodes in all directions and then extracting a triangle. An error may also increase with the degree of smoothing. Moreover, it is necessary to store and load a huge amount of triangle mesh data on the face, the bones, the nasal cavity, and the like.

As another example, Korean Patent No. 10-2041524 (Patent Document 2) directed to a method of manufacturing a customized three-dimensional implant discloses that values classified according to the degree of light and shade are converted into stereo-lithography (STL) files for three-dimensional imaging using a two-dimensional image that is part of a CT image and that a three-dimensional object including a cartilage is thus manufactured. However, when data are stored in an STL file format, a file size is considerably large. Furthermore, it takes considerably much time to convert an STL file or the like into a different file format necessary for an operator to perform processing.

In both Patent Documents 1 and 2, the bone and the nasal cavity are segmented on the basis of general CT data, and a shape that is the same as a shape of the cartilage is arbitrarily designed in such a manner as to be positioned over the naval cavity. However, during nasal surgery, an adjustment of the cartilage is necessary to alter the shape of the end of the nose. The result of the nasal surgery varies with a method of making an adjustment to the cartilage. However, in both Patent Documents 1 and 2, transformation of the cartilage is not given sufficient consideration. There is a limit in predicting the result of the nasal surgery, and thus it is difficult to design a nasal implant precisely customized for a patient.

In addition, in both Patent Documents 1 and 2, a bottom surface of the nasal implant is designed on the basis of the designed cartilage, but an external line of the nasal implant other than the bottom surface thereof is not given sufficient consideration. Usually, a design of the nasal implant is an important factor in determining the patient's satisfaction of the nasal surgery because the shape of the nose that results from the nasal surgery is determined by the external line of the nasal implant other than the bottom surface thereof. Particularly, a variety of molding product lines of ready-made nasal implants categorized by a height, a length, and an external line in the related art are available. Therefore, customized nasal implants in the related art, which are manufactured as described in Patent Documents 1 and 2, are less competitive in design than the variety of molding product lines of ready-made nasal implants. In some cases, for reflection in the design of the nasal implant, a nasal implant manufacturing company may perform selection from among numerical data on a height, a length, a width, a shape, and the like of the nasal implant. However, only the simple use of these numerical values makes it difficult not only to determine a stereoscopic shape of the entire nasal implant simply, but also to reflect characteristics of each patient. Thus, the result of the nasal surgery is difficult to predict.

Moreover, it takes much time to, for example, design, place an order with, and consult about a customized nasal implant. A CT image of a patient is captured in a hospital, and the captured CT image is sent to a manufacturer. The manufacturer sends data on a cartilage designed on the basis of CT data. A doctor in the hospital consults with the patient about the designed cartilage and then performs an operation on the patient's nose. To this end, the patient needs to visit the hospital at least two times. These processes are inefficient.

The shape of the nose that results from the nasal surgery is determined by a doctor's surgical capability and aesthetic sense. Therefore, a nasal implant design of manufacturing a patient-customized nasal implant is necessary to reflect many factors that influence the result of the nasal surgery.

The foregoing is intended merely to aid in the understanding of the background of the present disclosure, and is not intended to mean that the present disclosure falls within the purview of the related art that is already known to those skilled in the art.

DOCUMENTS OF RELATED ART (Patent Document 1): Korean Patent Application Publication No. 10-2019-0131796
(Patent Document 2): Korean Patent No. 10-2041524

SUMMARY OF THE INVENTION

An objective of the present disclosure is to solve the above-described problems in the related art and to provide a technical solution that has been requested.

Particularly, another objective of the present disclosure is to provide a nasal implant design method of manufacturing a patient-customized nasal implant through an adjustment to a cartridge that is based on nasal cartridge data learned through artificial intelligence.

According to an aspect of the present disclosure, there is provided a nasal implant design method of manufacturing a patient-customized nasal implant, the nasal implant design method including: (a) acquiring a medical image of a patient's nasal portion; (b) automatically realizing a three-dimensional volume rendering image, including the skin, the bones, and the cartilage of a nasal portion, from the medical image of the patient's nasal portion on the basis of nasal cartilage data learned through artificial intelligence; (c) simulating the nasal cartilage with the three-dimensional volume rendering image in such a manner as to be suitable for a patient; (d) stably nesting a nasal implant selected from an imaginary nasal implant model database on the simulated nasal cartilage and the nasal bones; and (e) simulating the stably nested nasal implant and designing a patient-customized nasal implant in such a manner as to be suitable for the patient.

In the nasal implant design method, in (a) the acquiring of the medical image, the medical image may be a CT image resulting from low-dose radiation exposure or a cone beam computed tomography (CBCT) image resulting from low-dose radiation exposure.

In the nasal implant design method, (b) the automatic realizing of the three-dimensional volume rendering image may include predicting the nasal cartilage from the medical image of the patient's nasal portion on the basis of the nasal cartilage data learned through a machine learning scheme or a deep learning scheme using a medical image resulting from high-dose radiation exposure from which the nasal cartilage is visible.

In the nasal implant design method, (c) the simulating of the nasal cartilage may include: (c-1) selecting a skin thickness from a plurality of choices; (c-2) cutting off respective portions of the nasal cartilage and the nasal bones depending on whether or not to rasp a hump portion; (c-3) setting an amount of movement of the nasal cartilage depending on whether or not to perform an operation on a nasal tip; and (c-4) naturally correcting an external line of the nasal cartilage, wherein (c-1) the selecting of the thickness, (c-2) the cutting-off of the respective portions, and (c-3) the setting of the amount of movement may be performed regardless of order.

In the nasal implant design method, in (e) the simulating of the stably nested nasal implant, a width of the patient-customized nasal implant may be automatically adjusted according to the selected skin thickness in (c-1) the simulating of the nasal cartilage.

In the nasal implant design method, depending on a doctor's determination, it may be determined whether or not (c-2) the cutting-off of the respective portions of the nasal cartilage and (c-3) the setting of the amount of movement are performed.

In the nasal implant design method, in (c-3) the setting of the amount of movement, as the nasal cartilage is moved, the skin thickness may be automatically adjusted.

In the nasal implant design method, (c-4) the natural correcting of the external line may be performed by filling a space between the upper lateral cartilage and the lower lateral cartilage that constitute the nasal cartilage.

In the nasal implant design method, (d) the stable nesting of the nasal cartilage may include: (d-1) marking a nasal tip reference point and a variable point in a middle of a forehead on the three-dimensional volume rendering image including the simulated nasal cartilage; (d-2) selecting the nasal implant from a database containing various types of imaginary nasal implant models; and (d-3) stably nesting the selected nasal implant on the simulated nasal cartilage and the nasal bones in a manner that aligns at an angle to a line connecting the nasal tip reference point and the variable point in the middle of the forehead that are marked on the three-dimensional volume rendering image.

In the nasal implant design method, the variable point in the middle of the forehead may be selected from among points between a nasion and a point that is positioned 20 mm upward away from the nasion.

In the nasal implant design method, in (d-3) the stable nesting of the selected nasal implant, the nasal implant may be brought into contact with the simulated nasal cartilage and the nasal bones in a manner that is automatically bent inward with respect to the hump in a direction in which lower and upper portions thereof face each other.

In the nasal implant design method, (e) the simulating of the stably nested nasal implant may include: (e-1) adjusting a length, a width, an angle, and a thickness of the nasal implant; and (e-2) checking whether or not the nasal implant is brought into contact with the simulated nasal cartilage and the nasal bones, wherein when the nasal implant is not brought into contact with the simulated nasal cartilage and the nasal bones, and thus an empty space is formed, automatically filling the empty space; and when the nasal implant is not brought into contact with the simulated nasal cartilage and the nasal bones, and thus an overlapping portion is present, adjusting only a shape of the nasal implant except for the nasal cartilage and the nasal bones.

In the nasal implant design method, in (e-1) the adjusting of the length, the width, the angle, and the thickness, the angle of the nasal implant may be adjustable by being increased by an increment of 0.2 degrees or 0.5 degrees or being decreased by a decrement of 0.2 degrees or 0.5 degrees within a range from 0 to 5 degrees to the left side of the line connecting the nasal tip reference point and the variable point in the middle of the forehead and within a range from 0 to 5 degrees to the right side thereof.

The nasal implant design method, wherein subsequently to (e) the simulating of the stably nested nasal implant, may further include: (f) cutting an arbitrary surface of the patient-customized nasal cartilage and verifying whether or not the patient-customized nasal cartilage is perfectly brought into contact with the simulated nasal cartilage and the nasal bones; and (g) automatically computing and displaying a change in a height of a skin surface of the nasal portion with respect to the patient-customized nasal implant.

In the nasal implant design method, information on the designed patient-customized nasal implant may be stored in an encoded binary file format.

According to the present disclosure, the nasal cartilage may be automatically volume-rendered from the medical image of the patient on the basis of the nasal cartilage data learned through the artificial intelligence without performing a triangle mesh data operation through segmentation. Accordingly, the probability of occurrence of an error is reduced, and thus the degree of precision can be increased. Furthermore, a storage capacity necessary to perform processing can be reduced. As a result, the simplicity and economic feasibility of the design of the nasal implant are ensured.

According to the present disclosure, the simulation may be performed with the three-dimensional volume rendering image in such a manner as to be suitable for the patient. Accordingly, a predictive value of the result of the nasal surgery can be increased.

According to the present disclosure, the nasal implant selected from the imaginary nasal implant model database may be simulated in such a manner as to be suitable for the patient. Thus, not only can the patient's request be precisely reflected, but also aesthetic pleasure can be provided.

According to the present disclosure, the process in which the patient-customized nasal implant is designed through consulting with the doctor after acquiring the medical image of the patient's nasal portion is completed by visiting the doctor at least one time. Thus, it is possible to save time and also promote efficiency.

BRIEF DESCRIPTION OF THE DRAWINGS

The above and other objectives, features, and other advantages of the present disclosure will be more clearly understood from the following detailed description when taken in conjunction with the accompanying drawings, in which:

FIG. 10 is a view illustrating a state (the left side thereof) where the patient-customized nasal implant according to the present disclosure is not yet inserted and a state (the right side thereof) where imaginary plastic surgery is completed after the patient-customized nasal implant is inserted;

FIGS. 11-13 are flow diagrams of nonlimiting embodiments of the inventive method.

DETAILED DESCRIPTION OF THE INVENTION

Figure 1:
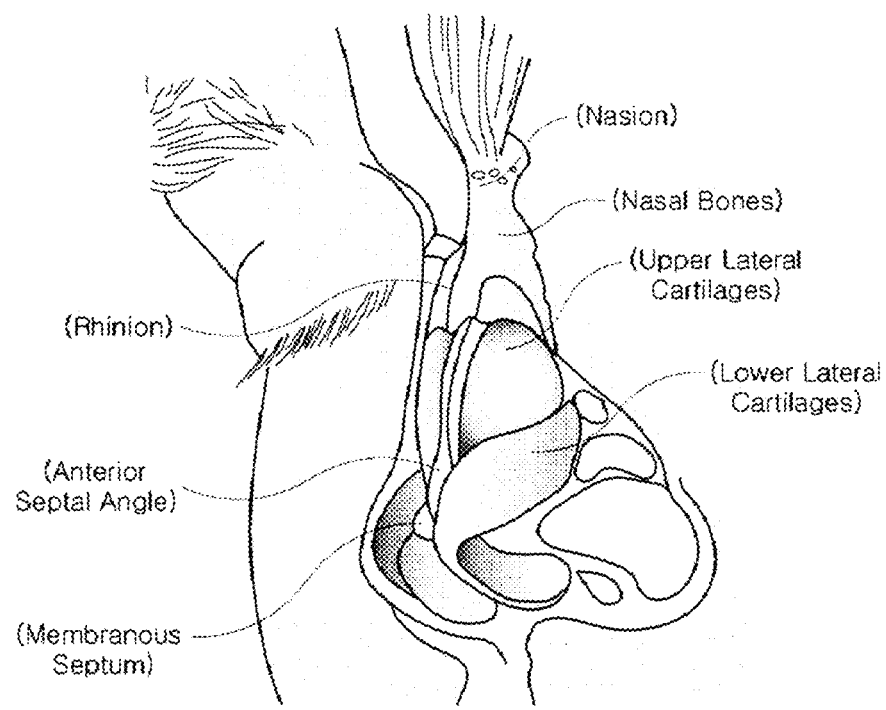
FIG. 1 is a view illustrating an anatomical structure of the nose.

An embodiment of the present invention will be described in detail below with reference to the drawings.

There is provided a nasal implant design method of manufacturing a patient-customized nasal implant according to the present invention, the nasal implant design method including: (a) a step of acquiring a medical image of a patient's nasal portion; (b) a step of automatically realizing a three-dimensional volume rendering image, including the skin, the bones, and the cartilage of a nasal portion, from the medical image of the patient's nasal portion on the basis of nasal cartilage data learned through artificial intelligence; (c) a step of simulating the nasal cartilage with the three-dimensional volume rendering image in such a manner as to be suitable for a patient; (d) a step of stably nesting a nasal implant selected from an imaginary nasal implant model database on the simulated nasal cartilage and the nasal bones; and (e) a step of simulating the stably nested nasal implant in such a manner as to be suitable for the patient and designing a patient-customized nasal implant.

In the step (a), the medical image of the patient's nasal portion may be acquired.

The "nasal portion" here means only a nasal portion in a narrow sense, but may mean an entire facial portion including a nose in a broad sense.

The medical image may be acquired through CT, CBCT, X-ray, MRI, PET, 3D Scanner, or the like, but is not limited to images acquired by these types of equipment. Specifically, the medical image may be a CT image or a CBCT image.

Usually, the CT image or the CBCT image that is used in a plastic surgery hospital or the like is obtained through low-dose radiation exposure. A medical image resulting from low-dose radiation exposure has a lower resolution than a medical image resulting from high-dose radiation exposure. However, the medical image resulting from low-dose radiation exposure can not only minimize an amount of radiation exposure, but also can cost by one-tenth or less of that of the medical image resulting from high-dose radiation exposure. For this reason, in most cases, the medical image resulting from low-dose radiation exposure is used in small- and medium-sized hospitals, such as a plastic surgery hospitals. A difference in the amount of radiation exposure between the medical image resulting from low-dose radiation exposure and the medical image resulting from high-dose radiation exposure are known in the art to which the present disclosure pertains. For example, this difference is disclosed in the following document: Christner J A, Kofler J M, McCollough C H, "Consequences of adopting International Commission on Radiological Protection publication 103 or dual energy scanning", AJR Am J Roentgenol, 2010; 194:881-889. According to this document, for example, the amount of radiation exposure necessary for the medical image resulting from low-dose radiation exposure may be equal to or larger than 0.1 mGv, but is smaller than 2.5 mGv. The amount of radiation exposure necessary for the medical image resulting from high-dose radiation exposure may be equal to or larger than 2.5 mGv, but is smaller than 1,000 mGv.

However, in the medical image resulting from low-dose radiation exposure, the nose skin, the nasal bones, the nasal cavity, and the like may be identified, but the nasal cartilage cannot be identified. Thus, a process of designing the nasal cartilage is necessary. In contrast, in the medical image resulting from high-dose radiation exposure, the nasal cartilage, as well as the nose skin, the nasal bones, and the nasal cavity, may be identified. This process of identifying the nasal cartilage is repeatedly learned through a machine learning scheme or a deep learning scheme, and thus the nasal cartilage data can be obtained.

As a result of the research or development efforts, the inventors discovered that, when nasal cartilage data obtained through artificial intelligence-guided learning were applied to a CT image resulting from low-dose radiation exposure or a CBCT image resulting from low-dose radiation exposure, a shape of the then-invisible cartilage, particularly, a thickness thereof could be identified. Subsequently, in the step (b), the three-dimensional volume rendering image, including the skin, bone, and cartilage of the nasal portion, may be automatically realized from the medical image of the patient's nasal portion on the basis of the nasal cartilage data learned through the artificial intelligence.

Figure 2A:
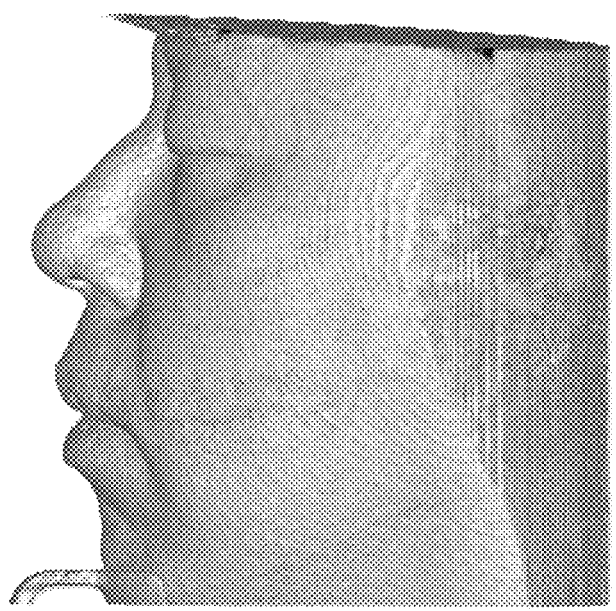
FIG. 2A is a view illustrating a three-dimensional volume rendering image realized from a medical image of a patient's nasal portion, particularly illustrating a skin surface.
Figure 2B:
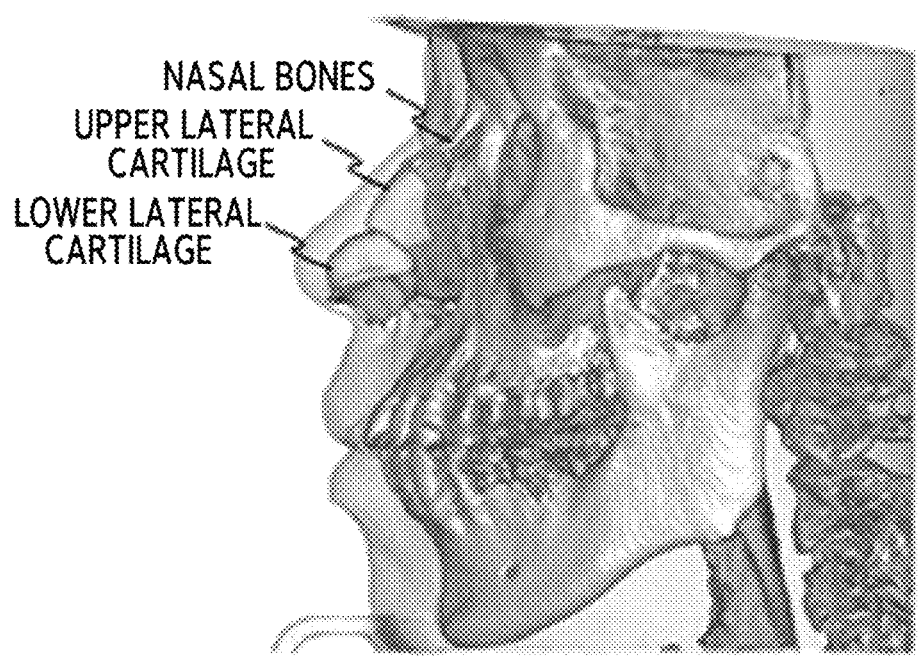
FIG. 2B is a view illustrating a three-dimensional volume rendering image realized from the medical image of the patient's nasal portion, particularly illustrating the bones, cartilage, and the nasal bones.

In this regard, FIGS. 2A and 2B are views each illustrating the three-dimensional volume rendering image realized from the medical image of the nasal portion of the patient. Particularly, from FIG. 2B, it can be seen that the upper lateral cartilage and the lower lateral cartilage are identified.

That is, for correcting and storing, triangle mesh data on the skin, the bones, and the nasal cavity are not extracted through segmentation. According to the present disclosure, a stereoscopic image including the nasal cartilage is realized while an original shape of the patient's nasal portion is maintained as is, through volume rendering that projects three-dimensional voxel data from the medical image of the nasal portion of the patient into a two-dimensional image. Then, a nasal implant is designed on the basis of the realized stereoscopic image. Therefore, the process of arbitrarily generating the cartilage over the nasal cavity is unnecessary. Thus, the degree of precision can be increased due to reduction of the probability of occurrence of an error, and a storage capacity necessary to perform processing can be reduced. As a result, the simplicity and economic feasibility of the design of the nasal implant are ensured.

The three-dimensional volume rendering image may be automatically generated without involvement of an operation when data on the medical image of the patient's nasal portion are uploaded into a related software application.

A shape of an end of a nose in which the nasal cartilage is positioned is an important factor in determining the patient's satisfaction of the nasal surgery. Therefore, during the nasal surgery it is necessary to make an adjustment to the cartilage that reflects the patient's characteristics. Accordingly, according to the present disclosure, the step (c) may include a step of simulating a position and shape of the nasal cartilage with the three-dimensional volume rendering image in such a manner as to be suitable for the patient. Thus, the position and shape of the nasal cartilage may be simulated in such a manner as to be suitable for the patient. Accordingly, a predictive value of the result of the nasal surgery can be increased.

Specifically, the simulation of the nasal cartilage may be configured to include: a step (c-1) of selecting a skin thickness from a plurality of choices; a step (c-2) of cutting off respective portions of the nasal cartilage and the nasal bones depending on whether or not to rasp a hump portion; a step (c-3) of setting an amount of movement of the nasal cartilage depending on whether or not to perform an operation on a nasal tip; a step (c-4) of naturally correcting an external line of the nasal cartilage.

First, although the nasal implant having the same width and the same thickness is inserted, there is a likelihood that the width of the nasal implant will look different in appearance according to a thickness of the patient's skin. Therefore, in a case where the thickness of the patient's skin is large, there is a need to reduce the width of the nasal implant. Accordingly, in the step (c-1), the skin thickness may be selected from the plurality of choices in each of which a skin thickness is stated quantitatively or qualitatively. For example, the plurality of choices may include the choice "a skin thickness is somewhat small/somewhat normal" and the choice "a skin thickness is somewhat large". One of the two choices may be selected. However, the present disclosure is not limited to these choices. At this point, when the choice "a skin thickness is somewhat large" is selected, the width of the customized nasal implant that is to be designed later may be automatically reduced by 0.3 to 0.5 mm, particularly, 0.4 mm than that of a final product. These numerical values are optimal values that are obtained by the inventors, considering the results of the numerous researches conducted and the surgical data from the aesthetic point of view and in terms of functions.

Figure 3A:
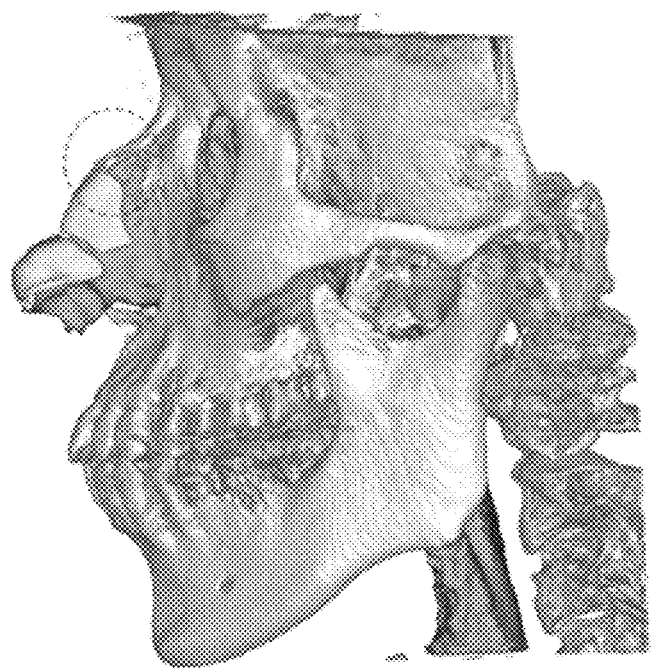
FIG. 3A is a view illustrating a pre-rasping hump portion.
Figure 3B:
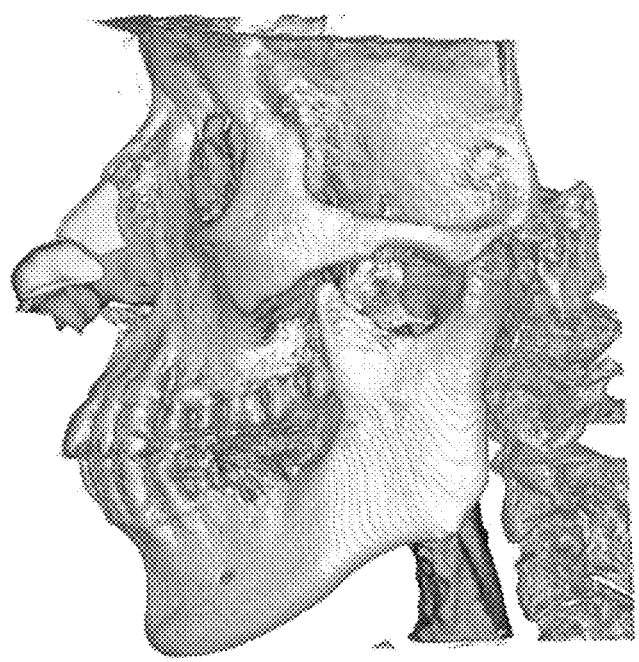
FIG. 3B is a view illustrating a post-rasping hump portion.

In a case where a patient has a prominent nose in which a hump is formed on an external line of a cartilage, there is a need to rasp respective portions of the nasal cartilage and the nasal bones in such a manner that the external line of the cartilage is smooth (a rasping process). Accordingly, in the step (c-2), through the process of rasping a hump portion, a curved surface of the cartilage may be flattened, and thus the hump may be naturally removed. In this regard, FIG. 3A is a view illustrating a pre-rasping hump portion, and FIG. 3B is a view illustrating a post-rasping hump portion. The hump is a portion indicated by a red-colored circle in FIG. 3A.

However, regardless of whether or not a patient does not have a prominent nose, a bottom of the nasal implant coming into contact with the external line of the cartilage may be rasped according to the doctor's selection. Thus, depending on a doctor's determination, it may be determined whether or not to perform the step (c-2).

Figure 4:
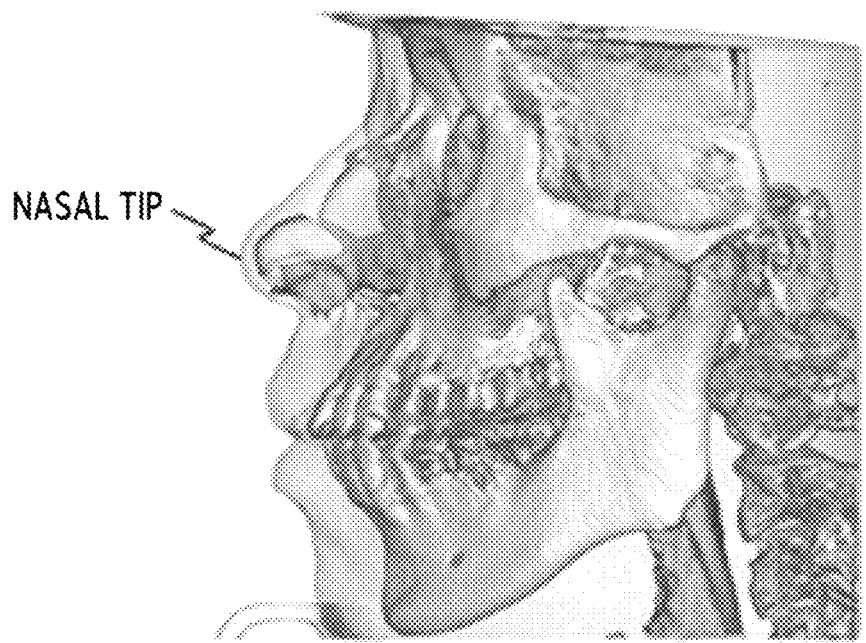
FIG. 4 is a view illustrating a lower lateral cartilage moved upward.
Figure 5:
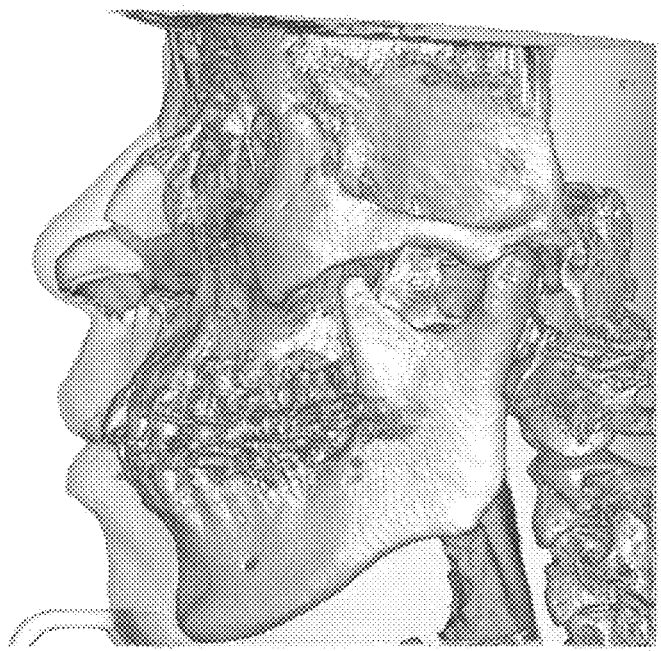
FIG. 5 is a view illustrating the lower lateral cartilage moved downward.

The shape of the end of the nose on which the cartilage is positioned is an important factor in determining the patient's satisfaction of the nasal surgery. In the step (c-3), a shape and position of the highest portion of the nose, that is, a shape and position of the nasal tip, may be changed by making an adjustment to the lower lateral cartilage. The lower lateral cartilage includes a left lower lateral cartilage and a right lower lateral cartilage. When the left and right lower lateral cartilage are combined, the moving direction and distance of the cartilage may be computed. For example, the lower lateral cartilage may be moved upward by 1 to 12 mm in such a manner that the nose tip is raised. Furthermore, the lower lateral cartilage may be moved downward in order to increase the length of a short nose. An angle change is also possible when the lower lateral cartilage is moved. In this regard, FIG. 4 is a view illustrating a state where the nasal tip is raised after the lower lateral cartilage is moved upward, and FIG. 5 is a view illustrating a state where the nasal tip is lowered after the lower lateral cartilage is moved downward.

Figure 6A:
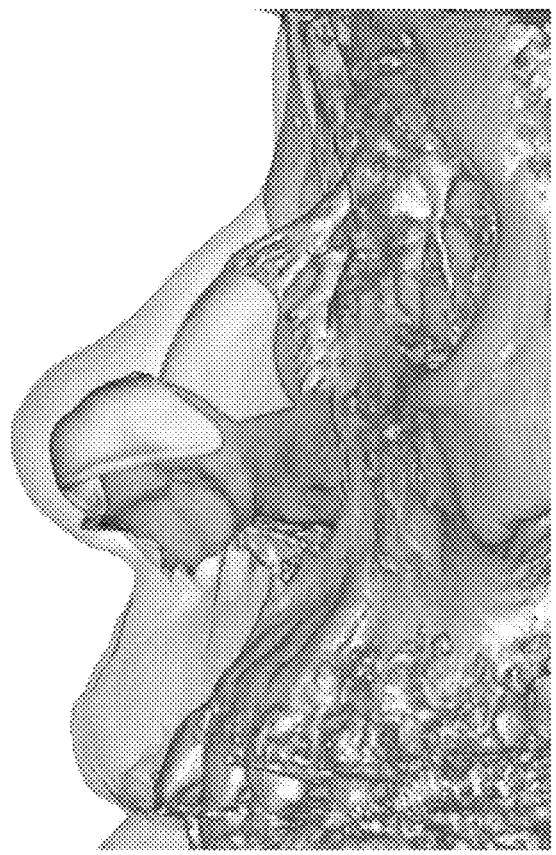
FIG. 6A is a view illustrating a change that results from moving the lower lateral cartilage upward.
Figure 6B:
FIG. 6B is a view illustrating a change that results from moving the lower lateral cartilage downward.

Accordingly, as the lower lateral cartilage is moved, the skin is moved together. Thus, the skin thickness is automatically adjusted. In this regard, FIG. 6A is a view illustrating a change that results from moving the lower lateral cartilage upward, and FIG. 6B is a view illustrating a change that results from moving the lower lateral cartilage downward. For example, when the lower lateral cartilage is moved upward by approximately 4 mm, the skin thickness is decreased by approximately 1 mm. The reason for this is because the skin is under tension due to the nasal cartilage to be inserted later.

Depending on the doctor's determination based on the patient's characteristics, it may be determined whether or not to perform the operation on the nasal tip.

The step (c-1) to step (c-3) may be performed regardless of order. Subsequently, in the step (c-4), the external line of the nasal cartilage may be naturally smoothened by filling a space between the upper lateral cartilage and the lower lateral cartilage that constitute the nasal cartilage.

Subsequently, in the step (d), the nasal implant is stably nested on the nasal cartilage simulated through the steps described above and the nasal bones.

Specifically, the step (d) includes: a step (d-1) of marking a nasal tip reference point and a variable point in the middle of a forehead on the three-dimensional volume rendering image including the simulated nasal cartilage; a step (d-2) of selecting the nasal implant from a database containing various types of imaginary nasal implant models; and a step (d-3) of stably nesting the selected nasal implant on the simulated nasal cartilage and the nasal bones in a manner that aligns at an angle to a line connecting the nasal tip reference point and the variable point in the middle of the forehead that are marked on the three-dimensional volume rendering image.

In the step (d-1), the nasal tip reference point may be an uppermost portion of the nose, and the variable point in the middle of the forehead may be selected from among points between a nasion that is the lowermost portion of the nose and a point that is positioned 20 mm upward away from the nasion. However, the nasal tip reference point and the variable point in the middle of the forehead may be moved according to the doctor's need.

As described above, the customized nasal implant in the related art results from designing a bottom surface of the nasal implant on the basis of the cartilage designed arbitrarily on the nasal cavity, but the external line of the nasal implant other than the bottom surface of the nasal implant is not given sufficient consideration. The customized nasal implants in the related art are less competitive in design than a variety of molding product lines of ready-made nasal implants. In contract, the nasal implant according to the present disclosure is selected from the imaginary nasal implant model database that is retained by the inventors, and thus design competitiveness thereof can be increased.

100 or more nasal implants for nasal surgery that constitute the imaginary nasal implant model database are categorized by height, length, and an external line into a variety of product lines. For more information, refer to Korean Patent No. 0759104 and Korean Registered Design Nos. 0729100, 0729098, 0398523, 0398523 (similar design No. 1), 0895587, 0895588, 0895589, 0895590, 0895591, 0895592, 0895593, 0895594, 0895595, 0895596, 0895597, 0895599, 0895600, 0895601, 0972134, and 0942611, for example.

However, the variety of product lines is not limited to Korean Patent and Korean Registered Designs that are mentioned above. The imaginary nasal implant model database may be stored in a library of a software application related thereto.

In the step (d-3), the selected nasal implant may be stably nested on the simulated nasal cartilage and the nasal bones in a manner that aligns at the angle to the line connecting the nasal tip reference point and the variable point in the middle of the forehead that are marked on the three-dimensional volume rendering image. In this case, for stable nesting, the nasal implant is brought into contact with the nasal cartilage and the nasal bones in a manner that is automatically bent inward with respect to the hump in a direction in which lower and upper portions thereof face each other. Accordingly, a space can be prevented from being formed between the nasal implant and the nasal cartilage, thereby preventing side effects such as inflammation. At this point, an angle at which the nasal implant is bent may be 1 to 15 degrees with respect to the line connecting the nasal tip reference point and the variable point in the middle of the forehead.

Figure 7A:
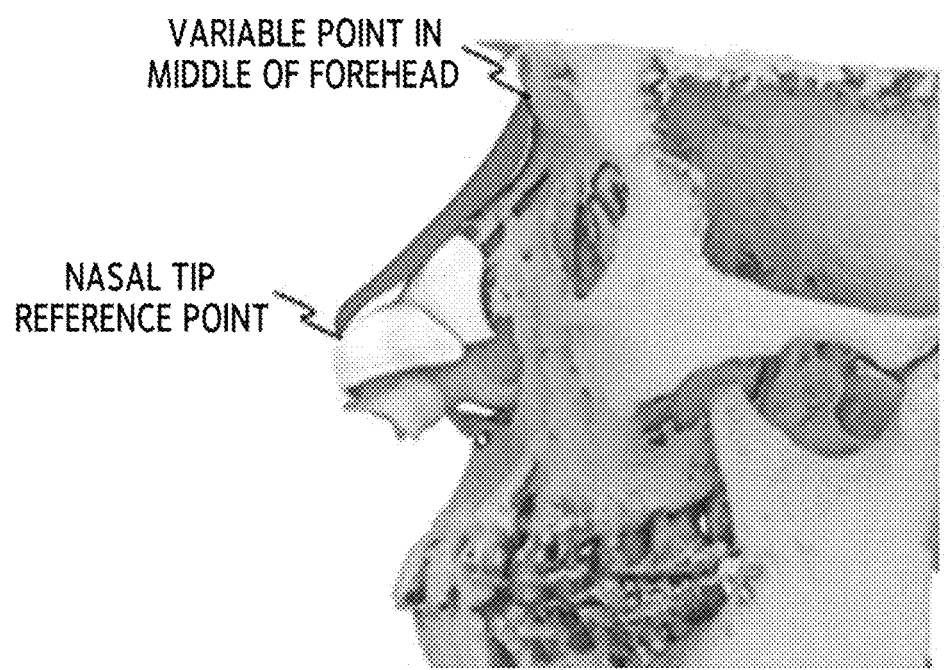
FIG. 7A is a view illustrating a state where a selected nasal implant is automatically stably nested on the previously simulated nasal cartilage and the nasal bones.
Figure 7B:
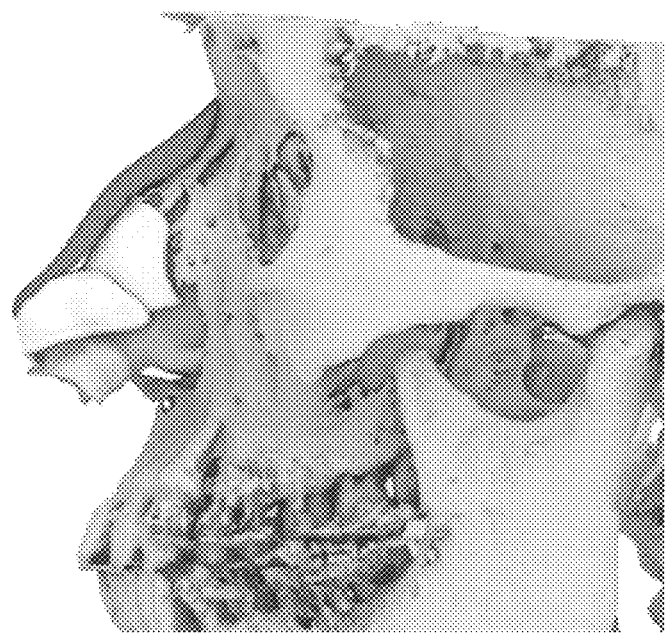
FIG. 7B is a view illustrating a state where, for stable nesting, the nasal implant is brought into contact with the nasal cartilage simulated in a bent manner and the nasal bones.

In this regard, FIG. 7A is a view illustrating a state where the nasal implant is automatically stably nested on the previously simulated nasal cartilage and the nasal bones. FIG. 7B is a view illustrating a state where, for stable nesting, the nasal implant is brought into contact with the nasal cartilage simulated in a bent manner and the nasal bones.

According to the present disclosure, an imaginary nasal implant may be selected from the imaginary nasal implant model database, may be stably nested on the nasal cartilage, and then the imaginary nasal implant may be simulated in such a manner as to be suitable for the patient. Thus, not only can the patient's request be precisely reflected, but also aesthetic pleasure can be provided.

Specifically, the step (e) may be configured to include: a step (e-1) of adjusting a length, a width, an angle, and a thickness of the nasal implant; and a step (e-2) where it is checked whether or not the nasal implant is brought into contact with the simulated nasal cartilage and the nasal bones, and where when the nasal implant is not brought into contact with the simulated nasal cartilage and the nasal bones, and thus an empty space is formed, the empty space is automatically filled, and when the nasal implant is not brought into contact with the simulated nasal cartilage and the nasal bones, and thus an overlapping portion is present, only a shape of the nasal implant except for the nasal cartilage and the nasal bones is adjusted.

In the step (e-1), the length, the width, and the angle, and the thickness of the nasal implant may be adjusted. This adjustment is possible by inputting a "number" and by using a "bar". When the adjustment is made by using the "bar", the length that changes may be expressed in millimeters. The angle of the nasal implant may be adjusted by being increased by an increment of 0.2 degrees or 0.5 degrees or being decreased by a decrement of 0.2 degrees or 0.5 degrees within a range from 0 to 5 degrees to the left side of the line connecting the nasal tip reference point and the variable point in the middle of the forehead and within a range from 0 to 5 degrees to the right side thereof. However, the angle of the nasal implant is not limited to this adjustment. When the length, the width, the angle, and the thickness of the nasal implant are adjusted, a change in the nasal implant may be verified with the unaided eye or with aided vision.

Figure 8:
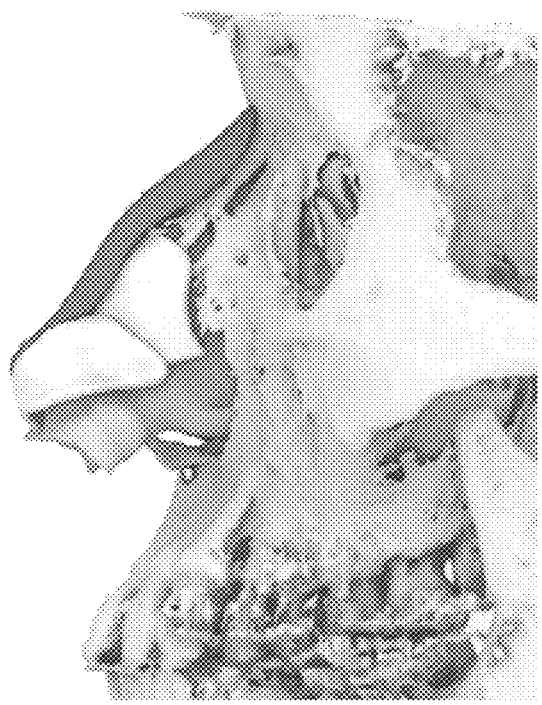
FIG. 8 is a view illustrating a state where the nasal implant fits the nasal cartilage illustrated in FIG. 7B after a length, a width, and a thickness thereof are adjusted.

Subsequently, in the step (e-2), it may be checked whether or not the nasal implant is brought into contact with the simulated nasal cartilage and the nasal bones. Furthermore, when the nasal implant is not brought into contact with the simulated nasal cartilage and the nasal bones, and thus an empty space is formed, the empty space may be automatically filled. Furthermore, when the nasal implant is not brought into contact with the simulated nasal cartilage and the nasal bones, and thus an overlapping portion is present, only a shape of the nasal implant except for the nasal cartilage and the nasal bones may be adjusted. This process may be performed using 3-D reconstruction and a Boolean operation. In this regard, FIG. 8 is a view illustrating a state where the nasal implant fits the nasal cartilage illustrated in FIG. 7B after the length, the width, and the thickness thereof are adjusted.

Subsequently to the step (e), the nasal implant design method of manufacturing a customized nasal implant customized to the present invention may further include: a step (f) of cutting an arbitrary surface of the patient-customized nasal cartilage and verifying whether or not the patient-customized nasal cartilage is perfectly brought into contact with the simulated nasal cartilage and the nasal bones; and an imaginary plastic surgical step (g) of automatically computing and displaying a change in a height of a skin surface of the nasal portion with respect to the patient-customized nasal implant.

Figure 9:
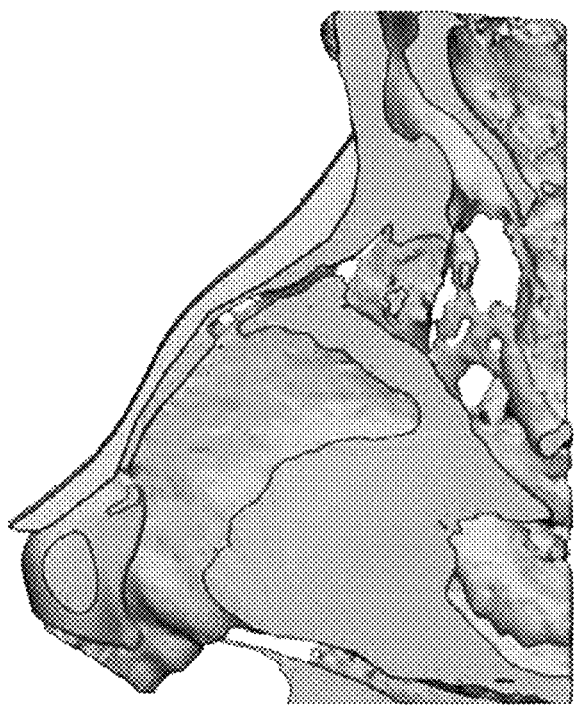
FIG. 9 is a cross-sectional view illustrating a patient's customized nasal implant stably nested.
Figure 12:
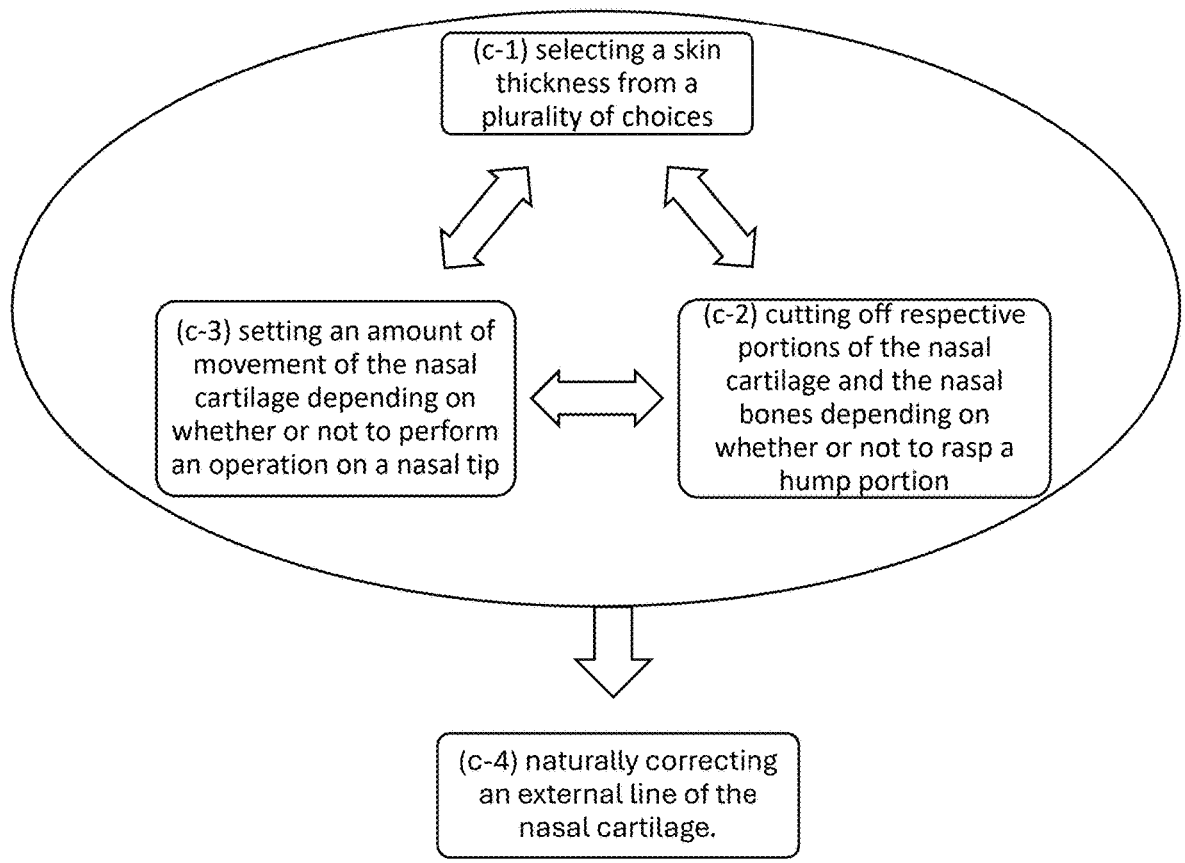
Figure 13:
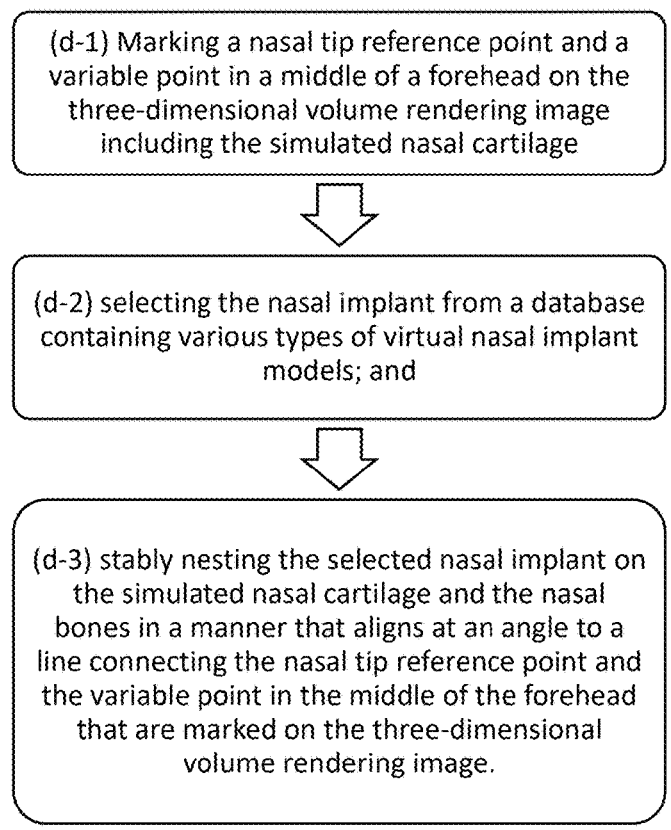

In the step (f), the arbitrarily cut surface of the patient-customized nasal implant may be verified with a line and thus it may be verified whether or not the nasal implant is completely brought into contact with the nasal cartilage and the nasal bones. At this point, a cutting direction may be a direction of the line connecting the nasal tip reference point and the variable point in the middle of the forehead. In this regard, FIG. 9 is a cross-sectional view illustrating a patient's customized nasal implant stably nested.

In the subsequent step (g), the change in the height of the skin surface of the nasal portion with respect to the patient-customized nasal implant that is completed through volume computation may be automatically computed and displayed. Thus, the imaginary plastic surgery may be completed. In this regard, FIG. 10 is a view illustrating a state (the left side thereof) where the patient-customized nasal implant according to the present disclosure is not yet inserted and a state (the right side thereof) where imaginary plastic surgery is completed after the patient-customized nasal implant is inserted.

When the steps described above are completed, information on the patient-customized nasal implant may be stored in an encoded binary file format instead of a stereo-lithography file format.

Usually, the STL file format is a standard format for storing the triangle mesh data, and data in the STL file format is readable by anyone. Copying, modifying, or editing of the data in the STL file format is possible. Thus, the data in the STL file format are vulnerable to intellectual property infringement actions, such as illegal copying, modifying, and editing. According to the present disclosure, data may be stored in the encoded binary file format, and thus security of the data can be enhanced. This encoding scheme is unlimited. However, for example, an encoding scheme in which data are encoded and stored in a state where the order of storing information is changed using a file storage time may be employed, and a decoding scheme in which the encoded data are decoded and stored in a memory in a state where the order of storing information is restored to the original order using the file storage time may be employed.

In this manner, according to the present disclosure, the process in which the patient-customized nasal implant is designed through consulting with the doctor after acquiring the medical image of the patient's nasal portion may be completed through the related program by visiting the doctor at least one time. Thus, it is possible to save time and also promote efficiency.

Although the specific embodiment of the present disclosure has been described for illustrative purposes, those skilled in the art will appreciate that various modifications, additions and substitutions are possible, without departing from the scope and spirit of the disclosure as disclosed in the accompanying claims.

What is claimed is:

1. A nasal implant design method of manufacturing a patient-customized nasal implant, the nasal implant design method comprising:
  (a) acquiring a medical image of a patient's nasal portion wherein the medical image is a computed tomography (CT) image resulting from low-dose radiation exposure or a cone beam computed tomography (CBCT) image resulting from low-dose radiation exposure;
  (b) automatically realizing a three-dimensional volume rendering image, including skin, bones, and cartilage of a nasal portion, from the CT image resulting from low-dose radiation exposure or a CBCT image resulting from low-dose radiation exposure of the patient's nasal portion on the basis of nasal cartilage data learned through artificial intelligence without performing a triangle mesh data operation through segmentation, wherein said automatic realizing comprises predicting the nasal cartilage from the medical image of the patient's nasal portion on the basis of the nasal cartilage data learned through a deep learning scheme using medical images resulting from high-dose radiation exposure from which the nasal cartilage is visible;
  (c) simulating the nasal cartilage with the three-dimensional volume rendering image;
  (d) stably nesting a nasal implant selected from a virtual nasal implant model database on the simulated nasal cartilage and the nasal bones;
  (e) simulating the stably nested nasal implant and designing a patient-customized nasal implant,
  (f) cutting an arbitrary surface of a patient-customized nasal cartilage from the patient-customized nasal implant and verifying whether or not the patient-customized nasal cartilage is brought into contact with the simulated nasal cartilage and the nasal bones; and
  (g) automatically computing and displaying a change in a height of a skin surface of the nasal portion with respect to the patient-customized nasal implant.

2. The nasal implant design method of claim 1, wherein (c) the simulating of the nasal cartilage comprises:
  (c-1) selecting a skin thickness from a plurality of choices;
  (c-2) cutting off respective portions of the nasal cartilage and the nasal bones depending on whether or not to rasp a hump portion;
  (c-3) setting an amount of movement of the nasal cartilage depending on whether or not to perform an operation on a nasal tip; and
  (c-4) naturally correcting an external line of the nasal cartilage,
  wherein (c-1) the selecting of the thickness, (c-2) the cutting-off of the respective portions, and (c-3) the setting of the amount of movement are performed regardless of order.

3. The nasal implant design method of claim 2, wherein in (e) the simulating of the stably nested nasal implant, a width of the patient-customized nasal implant is automatically adjusted according to the selected skin thickness in (c-1) the simulating of the nasal cartilage.

4. The nasal implant design method of claim 2, wherein in (c-3) the setting of the amount of movement, as the nasal cartilage is moved, the skin thickness is automatically adjusted.

5. The nasal implant design method of claim 2, wherein (c-4) the natural correcting of the external line is performed by filling a space between the upper lateral cartilage and the lower lateral cartilage that constitute the nasal cartilage.

6. The nasal implant design method of claim 1, wherein (d) the stable nesting of the nasal cartilage comprises:
 (d-1) marking a nasal tip reference point and a variable point in a middle of a forehead on the three-dimensional volume rendering image including the simulated nasal cartilage;
 (d-2) selecting the nasal implant from a database containing various types of virtual nasal implant models; and
 (d-3) stably nesting the selected nasal implant on the simulated nasal cartilage and the nasal bones in a manner that aligns at an angle to a line connecting the nasal tip reference point and the variable point in the middle of the forehead that are marked on the three-dimensional volume rendering image.

7. The nasal implant design method of claim 6, wherein the variable point in the middle of the forehead is selected from among points between a nasion and a point that is positioned 20 mm upward away from the nasion.

8. The nasal implant design method of claim 6, wherein in (d-3) the stable nesting of the selected nasal implant, the nasal implant is brought into contact with the simulated nasal cartilage and the nasal bones in a manner that is automatically bent inward with respect to a hump portion in a direction in which lower and upper portions thereof face each other.

9. The nasal implant design method of claim 6, wherein (e) the simulating of the stably nested nasal implant comprises:
 (e-1) adjusting a length, a width, an angle, and a thickness of the patient-customized nasal implant; and
 (e-2) checking whether or not the patient-customized nasal implant is brought into contact with the simulated nasal cartilage and the nasal bones,
 wherein when the patient-customized nasal implant is not brought into contact with the simulated nasal cartilage and the nasal bones, and thus an empty space is formed, automatically filling the empty space; and
 when the patient-customized nasal implant is not brought into contact with the simulated nasal cartilage and the nasal bones, and thus an overlapping portion is present, adjusting only a shape of the patient-customized nasal implant except for the nasal cartilage and the nasal bones.

10. The nasal implant design method of claim 9, wherein in (e-1) the adjusting of the length, the width, the angle, and the thickness, the angle of the patient-customized nasal implant is adjustable by being increased by an increment of 0.2 degrees or 0.5 degrees or being decreased by a decrement of 0.2 degrees or 0.5 degrees within a range from 0 to 5 degrees to the left side of the line connecting the nasal tip reference point and the variable point in the middle of the forehead and within a range from 0 to 5 degrees to the right side thereof.

11. The nasal implant design method of claim 1, wherein information on the designed patient-customized nasal implant is stored in an encoded binary file format.

* * * * *